US012778447B2

(12) United States Patent
Patel et al.

(10) Patent No.: US 12,778,447 B2
(45) Date of Patent: *Nov. 3, 2026

(54) CAPNOMETER

(71) Applicant: Cambridge Respiratory Innovations LTD, Cambridge (GB)

(72) Inventors: Nalinkumar Patel, Cambridgeshire (GB); Julian Carter, Cambridgeshire (GB); Benjamin Jeremy Walsh, Cambridgeshire (GB); Russell Overend, Glasgow (GB); Calum Mcgregor, Glasgow (GB); Des Gibson, Glasgow (GB); Ewan Waddell, Glasgow (GB)

(73) Assignee: TidalSense Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/361,157

(22) Filed: Jul. 28, 2023

(65) Prior Publication Data

US 2023/0363665 A1 Nov. 16, 2023

Related U.S. Application Data

(60) Continuation of application No. 17/095,635, filed on Nov. 11, 2020, now abandoned, which is a division of (Continued)

(30) Foreign Application Priority Data

Dec. 10, 2014 (GB) ..................................... 1421961

(51) Int. Cl.
*A61B 5/08* (2006.01)
*A61B 5/00* (2006.01)
(Continued)

(52) U.S. Cl.
CPC ............ *A61B 5/082* (2013.01); *A61B 5/0059* (2013.01); *A61B 5/0836* (2013.01); (Continued)

(58) Field of Classification Search
CPC ..... A61B 5/082; A61B 5/0059; A61B 5/0836; A61B 5/097; A61B 2560/0223; A61B 2560/0238; G01N 33/497; G01N 21/3504
See application file for complete search history.

(56) References Cited

U.S. PATENT DOCUMENTS 5,261,415 A * 11/1993 Dussault ............ G01N 21/3504 73/23.3
5,625,189 A * 4/1997 McCaul ............... G02B 6/4246 250/341.1

(Continued)

OTHER PUBLICATIONS

International Search Report and Written Opinion mailed Apr. 4, 2016, in connection with International Application No. PCT/GB2015/053779.

(Continued)

*Primary Examiner* — Andrey Shostak
(74) *Attorney, Agent, or Firm* — Wolf, Greenfield & Sacks, P.C.

(57) ABSTRACT

We describe a capnometer for detecting a concentration of a component in a gas, wherein said gas is inhaled and/or exhaled by a patient, said capnometer comprising: an air flow region through which said gas passes to and/or from said patient's lung; a mid-IR semiconductor emitter configured to provide IR light at a wavelength in the range 3-5 μm; a mid-IR semiconductor detector to detect said IR light; a reflector to reflect said IR light emitted by said emitter; wherein said emitter, said detector and said reflector are arranged such that said IR light emitted by said emitter passes through said air flow region via said reflector to said detector.

14 Claims, 5 Drawing Sheets

Related U.S. Application Data application No. 15/534,973, filed as application No. PCT/GB2015/053779 on Dec. 10, 2015, now abandoned.

(51) Int. Cl.

| | |
|---|---|
| ***A61B 5/083*** | (2006.01) |
| ***G01N 33/497*** | (2006.01) |
| *A61B 5/097* | (2006.01) |

(52) U.S. Cl.

CPC ............ *G01N 33/497* (2013.01); *A61B 5/097* (2013.01); *A61B 2560/0223* (2013.01); *A61B 2560/0238* (2013.01)

(56) References Cited

U.S. PATENT DOCUMENTS

| | | | | |
|---|---|---|---|---|
| 5,650,624 | A * | 7/1997 | Wong | G01N 21/3518 250/339.04 |
| 6,190,327 | B1 * | 2/2001 | Isaacson | A61B 5/0836 250/353 |
| 6,469,303 | B1 | 10/2002 | Sun et al. | |
| 6,599,253 | B1 | 7/2003 | Baum et al. | |
| 8,471,208 | B1 * | 6/2013 | Tang | G01N 21/05 250/341.1 |
| 2002/0026937 | A1 | 3/2002 | Mault | |
| 2003/0134427 | A1 | 7/2003 | Roller et al. | |
| 2007/0173731 | A1 * | 7/2007 | Meka | G01N 33/497 600/543 |
| 2011/0046500 | A1 * | 2/2011 | Haveri | A61B 5/0878 600/538 |
| 2012/0019767 | A1 * | 1/2012 | Cadet | G02B 1/18 427/164 |
| 2013/0271751 | A1 * | 10/2013 | Macgegor | G01N 21/3504 356/437 |
| 2014/0117238 | A1 | 5/2014 | McCann | |
| 2014/0194703 | A1 | 7/2014 | Wondka et al. | |
| 2014/0291526 | A1 | 10/2014 | Killich | |
| 2015/0034084 | A1 * | 2/2015 | Av-Gay | A61K 9/007 128/203.12 |
| 2018/0078175 | A1 | 3/2018 | Patel et al. | |
| 2021/0100478 | A1 | 4/2021 | Patel et al. | |

OTHER PUBLICATIONS

International Preliminary Report on Patentability mailed Jun. 22, 2017, in connection with International Application No. PCT/GB2015/053779.

* cited by examiner

CAPNOMETER

RELATED APPLICATIONS

This application is a Continuation of U.S. application Ser. No. 17/095,635, filed Nov. 11, 2020, entitled "CAPNOMETER", which is a Division of U.S. application Ser. No. 15/534,973, filed Jun. 9, 2017, entitled "CAPNOMETER", which is a national stage filing under 35 U.S.C. 371 of International Patent Application Serial No. PCT/GB2015/053779, filed Dec. 10, 2015, entitled "CAPNOMETER". Foreign priority benefits are claimed under 35 U.S.C. § 119(a)-(d) or 35 U.S.C. § 365(b) of British application number 1421961.2, filed Dec. 10, 2014. The entire contents of these applications are incorporated herein by reference in their entirety.

FIELD OF THE INVENTION

This invention generally relates to a capnometer, in particular a capnometer utilising a reflecting geometry, and methods for determining a $CO_2$ level in a gas using a capnometer.

BACKGROUND OF THE INVENTION

Non-dispersive infrared (IR) techniques utilise the 4.26 μm absorption band of $CO_2$ and are widely used in the gas analyser industry. Single collimated emission and detection at the 4.26 μm absorption band have been disclosed in, e.g. U.S. Pat. Nos. 4,423,739, 4,200,791, 4,013,260 and 3,893,770. In practice, this single beam configuration is rarely used due to output drifts as a result of temperature changes, instability of the individual components used, as well as contamination of windows enclosing the gas sample. Therefore, dual wavelength systems have been employed where the first wavelength is absorbed by $CO_2$, whereas the second wavelength is not absorbed by $CO_2$ and serves as a reference.

The use of a narrow band gap III-V material for optical absorption gas sensors has been described in US 2013/0271751 A1, WO 2007/091043 A1, and D. Gibson and C. MacGregor, "A Novel Solid State Non-Dispersive Infrared $CO_2$ Gas Sensor Compatible with Wireless and Portable Deployment", Sensors 2013, 13(6):7079-7103 (May 2013). A gas sensor using a cell structure with increased optical length by multiple reflections is specified in U.S. Pat. No. 4,322,621 and WO 2011/086394 A1.

However, there is a need for improving gas sensing in capnometers.

SUMMARY OF INVENTION

According to a first aspect of the invention, there is therefore provided a capnometer for detecting a concentration of a component in a gas, wherein said gas is inhaled and/or exhaled by a patient, said capnometer comprising: an air flow region through which said gas passes to and/or from said patient's lung; a mid-IR semiconductor emitter configured to provide IR light at a wavelength in the range 3-5 μm; a mid-IR semiconductor detector to detect said IR light; a reflector to reflect said IR light emitted by said emitter; wherein said emitter, said detector and said reflector are arranged such that said IR light emitted by said emitter passes through said air flow region via said reflector to said detector.

The capnometer may therefore be used to quantitatively measure the concentration (or associated temporal variation, as will be further described below) of a particular gas component in a gas mixture using the principle of non-dispersive IR absorption.

The reflecting geometry of the capnometer provides for low cost production and low power consumption. The inventors have realised that transmissive optics, rotating elements or beam splitter optics with filters, which are generally employed in a collimated optics geometry, may be made redundant in a capnometer by using the reflecting geometry. The capnometer may therefore be utilised to perform measurements in which an adjacent emitter/detector pair is arranged on one side of a gas sample volume and a reflecting surface is provided on the other side of the gas sample volume.

The reflecting geometry further allows for achieving an appropriate sampling length in order to achieve required signal-to-noise ratio in the detector at the gas concentration appropriate for lung function measurements. In the reflecting geometry, the sampling length may be determined by the distance between the emitter and the reflector as well as the distance between the reflector and the detector.

The capnometer may be operated in a non-diverting or substantially non-diverting mode so that high temporal resolution may be achieved when the concentration of the component in the gas is determined.

The capnometer may be implemented in a way which allows the measurement of a gas concentration close to the oro-nasal orifices.

In a preferred embodiment of the capnometer, the detection of the concentration of the component in a gas comprises detecting a temporal variation of the concentration of the component.

It will be appreciated that a number of configurations may be employed using the reflective geometry.

In a preferred embodiment of the capnometer, the emitter is located at a first location on a first side of said air flow region, the detector is located at a second location on a second side of said air flow region, and wherein said second side is opposite said first side from said air flow region.

Preferably, the reflector is located at a third location on a third side of said air flow region, wherein said third side is adjacent said first and second sides, respectively. The reflector may further be located at a fourth location on a fourth side of said air flow region, wherein said fourth side is opposite said third side from said air flow region. This may allow increasing the signal detected by the detector to improve the signal-to-noise ratio.

Alternatively, a geometry may be used in which the emitter is located at a first location on a first side of said air flow region, wherein said detector is located at a second location on a second side of said air flow region, wherein said first side is adjacent said second side, wherein said reflector is located at a third location on a third side of said air flow region, and wherein said third side is opposite said first side or opposite said second side.

It will be understood that a variety of configurations may be exploited in the reflective geometry of the capnometer. The relative locations of emitter, detector and reflector, and/or the shape of the reflector may be modified in order to ensure that IR light emitted by the emitter passes through the air flow region via the reflector to the detector.

In a preferred embodiment, the capnometer further comprises a breath tube, wherein the breath tube defines a channel between the emitter/detector and the reflector for the air flow region. Preferably, the breath tube is removable from the capnometer. This may be particularly useful since exchanging the breath tube after use may allow for minimising any contamination on the breath tube which could have an undesired impact on the measurements of the gas concentration.

In embodiments of the capnometer which use a breath tube, the emitter, the detector and the reflector may be mounted in the breath tube. Where the breath tube is removable from the capnometer, exchanging the breath tube with emitter, detector and reflector may allow for minimising any contamination on the emitter, detector and reflector.

In another preferred embodiment, the capnometer may further comprise an optical layer between the emitter and the reflector and/or between the detector and the reflector for improving a collection efficiency of the IR light emitted by the emitter onto the detector. This optical layer may comprise mid infrared transmissive material such as, but not limited to silicon. Other materials suitable for the optical layer will be known to those skilled in the art, and include, but are not limited to ZnS, ZnSe, Ge, chalocogenide glasses and certain polymers. It will be appreciated that where emitter and detector are arranged on the same side of the air flow region, the optical layer may be a single layer, or two separate layers between emitter/reflector and detector/reflector, respectively. Layer or layers may have anti-reflection coatings applied to their surfaces, thereby minimising or reducing reflection loss and maximising or increasing transmission through the layer or layers In a further preferred embodiment of the capnometer, the emitter and the detector are located external to the breath tube, and the breath tube comprises a mid-IR transmissive portion, wherein the mid-IR transmissive portion is aligned with the emitter and the detector to allow mid-IR light to pass therethrough into and out of the breath tube. Preferably, the mid-IR transmissive portion comprises a separate window. It will be understood that if no separate window is exploited, the breath tube may be mid-IR transmissive at the portion which is aligned with the emitter and the detector. Where the mid-IR transmissive portion comprises a separate window, the capnometer preferably further comprises a seal arranged between the breath tube and the separate window. The seal may be suitable for preventing air surrounding the capnometer from penetrating into the air flow region where the gas is sampled.

In a preferred embodiment of the capnometer, the mid-IR transmissive portion comprises an anti-reflection coating and/or an anti-fog coating. This may increase a collection efficiency of IR light emitted by the emitter onto the detector, and may therefore improve the signal-to-noise ratio as the coatings reduce scattering of IR light on the mid-IR transmissive portion. Alternatively, or additionally, the capnometer may further comprise a heater for heating the mid-IR transmissive portion. In this way, water condensation on the mid-IR transmissive portion may be prevented in order to increase the collection efficiency and hence the signal-to-noise ratio.

In addition to the mid-IR transmissive portion, in a preferred embodiment, the capnometer may further comprise an optical layer between the emitter and the reflector and/or between the detector and the reflector for improving a collection efficiency of the IR light emitted by the emitter onto the detector. It will be appreciated that where emitter and detector are arranged on the same side of the air flow region, the optical layer may be a single layer, or two separate layers between emitter/reflector and detector/reflector, respectively. Preferably, the optical layer comprises an anti-reflection coating and/or an anti-fog coating. More preferably, the capnometer may further comprise a second heater for heating the optical layer in order to avoid water condensation on the surface of the optical layer. It will be appreciated that the first heater and second heater may be integral. Furthermore, the mid-IR transmissive portion and the optical layer may, in embodiments, be integral.

As outlined above, the optical layer may comprise silicon, ZnS, ZnSe, Ge, chalocogenide glasses, certain polymers, or other materials known to those skilled in the art.

In embodiments where the emitter and the detector are external to the breath tube, the reflector may be mounted in the breath tube. Preferably, the reflector may comprise a coating on an inner surface of the breath tube, in particular an anti-reflection and/or an anti-fog coating.

It will be understood that a preferable type of coating (anti-reflection coating and anti-fog coating) may be determined dependent on the specific materials used for optical layer, reflector, mid-IR transmissive window and other components which may be in contact with the sampling gas.

In embodiments, the breath tube may comprise one or more alignment features for enabling the arrangement of the reflector with the emitter and the detector. Hence, these alignment features may improve a signal-to-noise ratio and reproducibility of the measurements taken with the capnometer. The one or more alignment features may comprise alignment pins which may provide kinematic location of the capnometer component parts and ease of assembly.

Alternatively, in embodiments of the capnometer, the reflector is located external to the breath tube, and the breath tube comprises a second mid-IR transmissive portion, wherein the second mid-IR transmissive portion is aligned with the reflector to allow mid-IR light to pass therethrough into and out of the breath tube.

In embodiments of the capnometer, the emitter may be configured to provide the IR light at two or more different wavelengths in the range 3-5 μm, and the detector may be configured to detect the two or more different wavelengths for the signal processor. This embodiment may be particularly suitable for detecting different gases with different absorption peaks or generally different absorption spectra.

In embodiments, the reflector may be mounted on an inner surface of the breath tube. The reflector may be integral to the breath tube or integral to a body of the capnometer. Alternatively, the capnometer may further comprise a reflector mounting for supporting the reflector.

In a preferred embodiment, the capnometer further comprises a memory to store the level data output. This may allow for analysing the gas concentration and/or temporal variation of the gas concentration measured with the capnometer at a later stage.

In a preferred embodiment, the gas component to be detected in the gas mixture is $CO_2$.

In a further preferred embodiment of the capnometer, the emitter comprises a III-V mid-IR semiconductor emitter.

In another preferred embodiment of the capnometer, the detector comprises a III-V mid-IR semiconductor detector.

It will be appreciated that the type of emitter and detector may be determined by the gas and/or gas component to be sampled.

In a preferred embodiment of the capnometer, the reflector comprises a reflective metal film coated with an organic layer. The organic layer may comprise an anti-fog coating, in particular where the reflector is arranged on an inner surface of the breath tube. Alternatively or additionally, a heater, e.g. one of the heaters specified above, may be provided in the capnometer for heating the organic layer to prevent water condensation on a surface of the organic layer.

It will be important to obtain a sufficient temporal resolution of the measurements to allow the signal to convey enough information about a perfusion and a ventilation of lungs of a patient. The sample width may be reduced using cut down optics and/or a breath tube design to accelerate gas through the sampling area. Therefore, in a preferred embodiment of the capnometer, the air flow region may have a cross-sectional area which is reduced where the IR light passes through the air flow region.

The capnometer may be used in combination with a medical device, wherein the capnometer further comprises blocking means to inhibit air surrounding the capnometer from flowing into the medical device.

In a preferred embodiment of the capnometer, the emitter comprises a plurality of emitters, wherein each of the plurality of emitters emits light centred at a different, respective wavelength.

This may allow different gases with different absorption spectra to be sampled with the capnometer. Furthermore, this embodiment allows for calibrating the device and/or determining when a measurement of a gas concentration is void, as will be further described below.

In a further preferred embodiment, the detector comprises a plurality of detectors, wherein each of the plurality of detectors detects light at a different, respective range of wavelengths.

The design of the optical path is to ensure a good collection efficiency of the optical system, comprising emitter and detector, employed in the capnometer. The use of materials with low absorption at wavelengths where the component absorbs light (e.g. 4.26 μm for $CO_2$) may be preferable. Moreover, a high reflective surface of the reflector may be achieved by using, e.g. Au deposited by physical vapour deposition or electrochemical deposition.

In a further aspect of the invention, there is provided a method of determining when a measurement of a $CO_2$ level in a gas exhaled by a patient in an inspiration/expiration cycle through a capnometer is void, the method comprising: measuring a $CO_2$ level in said gas during said inspiration using said capnometer; and determining that said measurement of said $CO_2$ level in said gas during said expiration is void when said measured $CO_2$ level in said gas during said inspiration is outside a first range of $CO_2$ levels.

Embodiments of the capnometer described herein may be used to implement this method.

In a preferred embodiment, the method further comprises determining a corrected $CO_2$ level in said gas during said expiration when said measurement has been determined to be void. Determining a corrected $CO_2$ level in the gas during the expiration may be achieved, for example, by correcting a signal detected by the detector and/or correcting for the light signal emitted by the emitter. Therefore, in a preferred embodiment, the correction is applied to one or both of a signal from an emitter of the capnometer and a signal from a detector of the capnometer. Various techniques to determine the corrected $CO_2$ level will be known to those skilled in the art.

In a related aspect of the invention, there is provided a method of determining when a measurement of a $CO_2$ level in a gas inhaled and/or exhaled by a patient in an inspiration/expiration cycle through a capnometer is void, the method comprising: providing said capnometer with a plurality of emitters, wherein each of said plurality of emitters emits light at a different, respective wavelength, wherein each of said different, respective wavelengths is within a detecting wavelength range of a detector of said capnometer; pulsing said plurality of emitters during a said inspiration and/or during a said expiration such that said light of each of said plurality of emitters is detected by said detector at a different, respective point in time; determining that the measurement is void when a scattering of said light emitted by said plurality of emitters correlates between at least two said emitters of said plurality of emitters.

Preferably, one of the plurality of emitters emits light substantially centred at 4.26 μm. Preferably, the method further comprises correcting a signal from the emitter which emits light substantially centred at 4.26 μm when the measurement is void. Alternatively or additionally, a signal from the detector may be corrected when the measurement is void.

The capnometer may be required to be calibrated in order for the output of the device, i.e. a $CO_2$ concentration, to meet accuracy requirements of a gas monitoring device, for example for medical application. Calibration may be performed in different ways, for example by providing a known gas concentration in the sampling area.

Therefore, in a further aspect of the invention, there is provided a method of calibrating a capnometer, the method comprising: providing a capnometer, in particular a capnometer as described in embodiments herein, providing a breath tube comprising a gas with a known $CO_2$ level; inserting said breath tube into said capnometer; measuring said $CO_2$ level of said gas in said breath tube using said capnometer; correlating said measured $CO_2$ level to said known $CO_2$ level; and storing said correlation in a memory of said capnometer.

The calibration may alternatively (or additionally) be performed by placing the capnometer in an area in which there may be no other source of $CO_2$ other than that of the atmospheric background (of, for example approximately 450 ppm), which we call zeroing.

Therefore, in a related aspect of the invention, there is provided a method of calibrating a capnometer, the method comprising: providing a capnometer, in particular a capnometer as described in embodiments herein, measuring, using said capnometer, a known $CO_2$ level of air surrounding said capnometer; correlating said measured $CO_2$ level to said known $CO_2$ level; and storing said correlation in a memory of said capnometer.

Although the signal which may be received by a detector in the capnometer may be affected by the $CO_2$ concentration between it and the emitter, the signal may also be affected by other absorbing and scattering materials in the path between emitter and detector, and/or drift in the emitter output and/or drift in the detector electronics. A reference channel may be used to compensate for these factors, which may take the form of an additional detector measuring at a wavelength to one side of the $CO_2$ absorption band that may be similarly affected by the same factors affecting the $CO_2$-centred detector. The inventors have realised that it is advantageous to avoid having to use a reference channel as regular zeroing may still be required as there may still be differences between the two channels.

Therefore, in a related aspect of the present invention, there is provided a method of calibrating a capnometer, the method comprising: providing a capnometer, in particular a capnometer as described in embodiments herein; measuring, using said capnometer, a $CO_2$ level of air surrounding said capnometer at two points in time before and after an exhaling-inhaling cycle of a user of said capnometer, to provide a first and second $CO_2$ background level input; and calibrating said capnometer based on a difference between said first and second $CO_2$ background level inputs.

We note that "user" and "patient" are used synonymously throughout the specification.

A capnometer using reflective optics may provide for a longer path length between emitter and detector and inherent stability of the emitter. These factors may allow realisation of a capnometer which may accurately measure $CO_2$ concentration at atmospheric background levels of $CO_2$.

For a capnometer which may be used as a personal medical or diagnostic device where the period of operation may be a few minutes long, it may be possible to measure the background $CO_2$ level at the beginning and end of the sample period and a difference in value may be due to some factor other than the $CO_2$ level.

By measuring the change in background over time, a correction may be applied to the capnometer $CO_2$ output.

In preferred embodiments, the background level is measured during the breath cycle when fresh air is drawn into the device. In this way, the device may be calibrated whilst being used.

In a preferred embodiment of the method, the $CO_2$ level of air surrounding the capnometer is measured before and after a plurality of the exhaling-inhaling cycles. This may advantageously allow for determining a $CO_2$ background level drift which may occur only slowly in time. The slow drift may be detected and the capnometer may be calibrated accordingly.

It will be appreciated that the $CO_2$ background level may be determined in between each exhaling-inhaling breath cycle by the user over a longer period of time, for example from the beginning of the use of the capnometer by the user to the end, i.e. the end of the last breath cycle. This may allow for calibrating the capnometer based on both sudden changes in the $CO_2$ background level and changes in the $CO_2$ background level which may occur over a (relatively) longer period of time.

In embodiments, the $CO_2$ background level is measured at different points in time after a predetermined number of exhaling-inhaling cycles has lapsed. Alternatively, the $CO_2$ background level may be measured with a predetermined time period in between the measurements, i.e. independent from the number of breath cycles.

In a further preferred embodiment of the method, air exhaled by the user exits the capnometer through a first part of the capnometer which is different to a second part of the capnometer through which air inhaled by the user enters the capnometer. This may be particularly useful when the $CO_2$ background level is measured before and after a single (or a few) exhaling-inhaling cycles. Embodiments therefore allow for minimising or reducing the deadspace (i.e. space in which exhaled air by the user is not entirely replaced with fresh inhaled air) in the capnometer so that the capnometer is fully (or almost fully) flushed with fresh inhaled air.

In order to achieve the above, the capnometer may comprise a diversion device. Therefore, in a related aspect of the present invention, there is provided a capnometer, in particular the capnometer as described in embodiments herein, comprising a diversion device for blocking one of a first and a second air-flow path in the capnometer at a time, wherein the first air-flow path connects an inhaling/exhaling portion of the capnometer at which a user of the capnometer inhales/exhales air and an intake portion of the capnometer through which air enters the capnometer, and wherein the second air-flow path connects the inhaling/exhaling portion and an exit portion of the capnometer at which air exits the capnometer.

In a preferred embodiment of the capnometer, the diversion device comprises a diverting valve which is controlled by the inhalation/exhalation of air by the user. For example, during inhalation, the diverting valve may open the first air-flow path between the inhaling/exhaling portion and the intake portion of the capnometer, while it closes the second air-flow path between the inhaling/exhaling portion and the exit portion of the capnometer at the same time.

The situation may be reversed during exhaling by the user, such that the connection between the inhaling/exhaling portion and the intake portion is closed, while the connection between the inhaling/exhaling portion and the exit portion is open. It will be appreciated that the opposite operation of the diverting valve may be employed, in which the first air-flow path is blocked during inhalation and the second air flow-path is open (and opposite during exhaling). The diverting valve may allow for a simple, reliable and cheap construction of the diversion device.

It will be understood that the diversion device may take other forms, which may be controlled by other means, such as electronic means.

It will be understood that two or more of the calibration methods described herein may be combined, in particular to provide for a more precise calibration of the capnometer.

Embodiments of the capnometer described herein may be combined with and/or incorporated into an inhaler. Therefore, there is provided an inhaler comprising a capnometer as described in any of the embodiments herein, wherein said capnometer is configured to monitor a $CO_2$ level in air inhaled through or exhaled through said inhaler.

In a further related aspect of the present invention, there is provided a system comprising a capnometer as described in embodiments herein, the capnometer configured to output gas concentration data from a gas inhaled/exhaled from a patient; and a data processor configured to receive the gas concentration data, and configured to perform any one of the methods according to embodiments described herein.

The gas concentration data may, in embodiments, be $CO_2$ gas concentration data.

It will be understood that the processor for receiving the gas concentration data and for performing any one (or more) of the methods described herein may be integral to the capnometer.

BRIEF DESCRIPTION OF THE DRAWINGS

These and other aspects of the invention will now be further described by way of example only, with reference to the accompanying figures, wherein like numerals refer to like parts throughout, and in which.

DETAILED DESCRIPTION OF PREFERRED EMBODIMENTS

Figure 1:
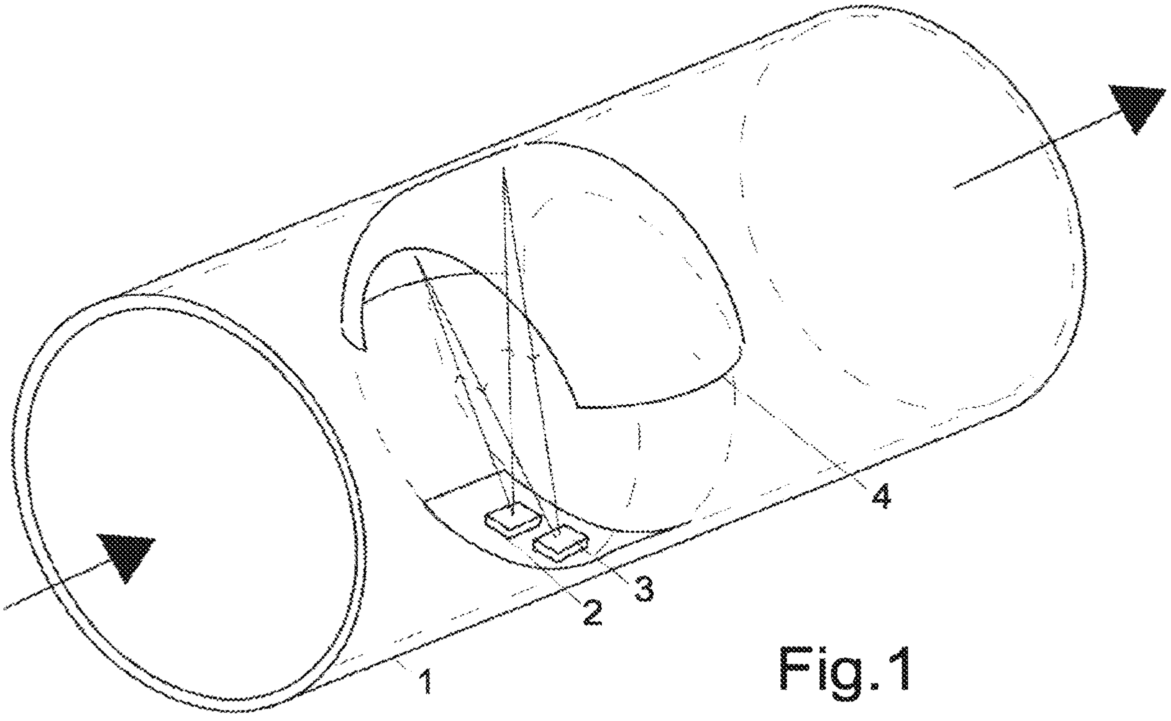
FIG. 1 shows a schematic illustration of components of a capnometer according to embodiments of the present invention.

FIG. 1 shows a schematic illustration of components of a capnometer according to embodiments of the present invention. The device may be exploited to measure the concentration of a gas component in a sample gas flowing across an air flow region interposed between an emitter (2)/detector (3) pair and a reflector (4). In this example, the emitter (2)/detector (3) pair and the reflector (4) are incorporated into a breath tube (1) and may be connected to a suitable electronic drive and detecting circuitry. The value of the detector current may be proportional to the emitter current and the amount of gas to be sampled in the sampling area.

The emitter (2) and/or the detector (3) of the capnometer may be composed of III-V semiconductors. It will be appreciated that materials suitable for emitter (2) and detector (3) will be known to those skilled in the art. In this example, an emitter diode is designed to emit IR radiation centred around 4.26 μm and the detector (3) is a photo-diode which has a peak sensitivity centred around 4.26 μm.

The path length traversed by the IR light emitted by the emitter (2) and detected by the detector (3) via the reflector (4) may be chosen such that the attenuation of the signal by absorption by $CO_2$ molecules is such that a change in intensity can be detected by the detector (3) for the concentration range that is appropriate for the gas stream. For human breath, the range of $CO_2$ concentration varies between the background $CO_2$ level which is inhaled by the human and up to 5% of gas which is exhaled by the human. In this case, the distance traversed by the IR light may be approximately 20 mm.

Figure 2:
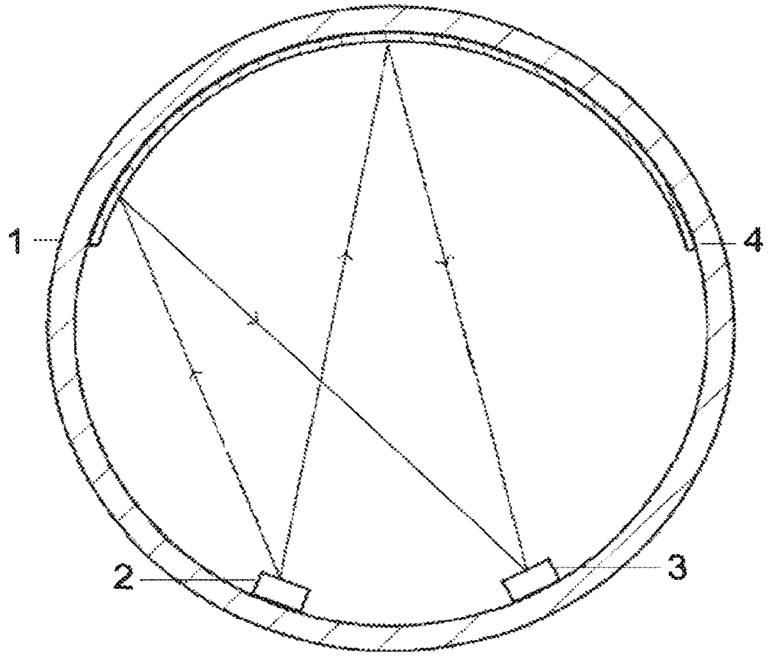
FIG. 2 shows a schematic cross-sectional view of components of a capnometer according to embodiments of the present invention.

As illustrated in the cross-sectional view of FIG. 2, the width of the sampled area may be determined by the distance between emitter (2)/reflector (4) and reflector (4)/detector (3). The width of the sampled area may be chosen such that the temporal resolution of the system is high enough for the intended application of the device. As outlined above, the air flow region may have a cross-sectional area which is reduced where the IR light passes through the air flow region to increase a time-resolution of the determination of the concentration of the gas component to be determined.

Figure 3:
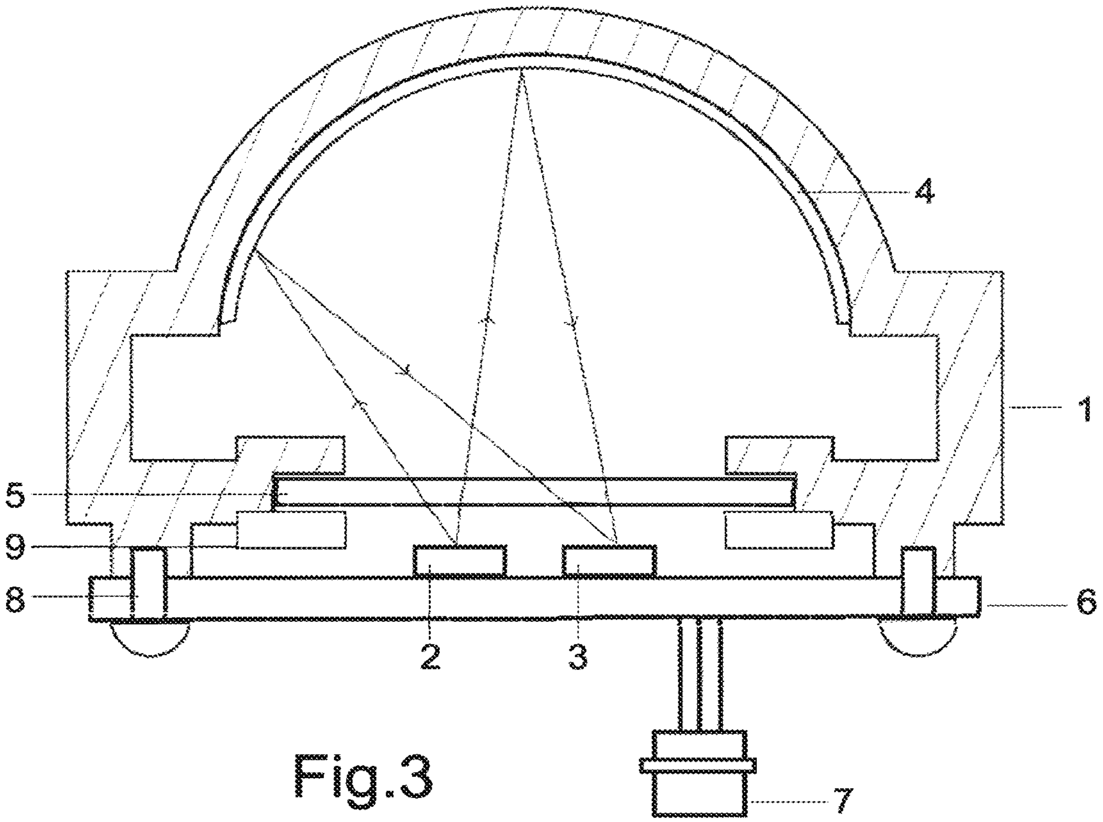
FIG. 3 shows a schematic of a capnometer comprising a silicon optic window according to embodiments of the present invention.

FIG. 3 shows a capnometer comprising a silicon optic window (5) according to embodiments of the present invention. The capnometer may be suitable for a single use. Alternatively, the capnometer may incorporate a disposable breath tube (1) with a reflector (4) and an optical layer (5) which may comprise silicon.

The breath tube (1) may be made from a high-density polymer which may have been injection moulded to form a reflector shape. The breath tube (1) may be coated, in this example by evaporation or via an electrochemical method, with a thin metal film which forms a reflector (4) with high reflection efficiency. It will be appreciated that a variety of deposition techniques known to the skilled person may be exploited. In this example, the high-density polymer breath tube (1) is coated with a gold film. It will be understood that a variety of materials known to those skilled in the art may be exploited for the breath tube (1) and the reflector (4), such as, but not limited to aluminium and silver.

The breath tube (1) may in embodiments contain channels which allow a sample gas to be diverted from the air flow region where the sample gas is examined, so that a conductance may be achieved which is high enough for the flow to be sampled.

In the example shown in FIG. 3, an optical layer (5) which may comprise silicon is provided opposite the reflector (4). The optical layer (5) may form a seal with the breath tube (1). The purpose of the optical layer (5) comprising silicon is both to protect the emitter (2)/detector (3) pair from breath, e.g. to avoid a contamination of the emitter (2)/detector (3) pair, and to increase the collection efficiency of the system by directing more light emitted from the emitter (2) to impinge on the detector (3). Other materials suitable for the optical layer (5) will be known to those skilled in the art, and include, but are not limited to ZnS, ZnSe, Ge, chalocogenide glasses and certain polymers. In this example, a gap is provided between the optical layer (5) and the emitter (2)/detector (3) pair. It will be appreciated that the optical layer (5) may alternatively be in contact with the emitter (2)/detector (3) pair. Furthermore, the optical layer (5) may comprise a plurality of layers between emitter (2) and reflector (4) and/or between detector (3) and reflector (4), respectively.

The capnometer may further comprise a seal (9) to prevent gas from the surrounding area from entering the sampling area. In this example, the seal (9) is arranged at two locations where the breath tube (1) and the optical layer (5) connect with each other. It will be appreciated that the seal (9) may be arranged at one or more locations. The seal (9) may be arranged on a side facing the air flow region where the breath tube (1) and the optical layer (5) connect, and/or on a side facing away from the air flow region (as shown in FIG. 3).

As outlined above, the optical layer (5) may comprise an anti-reflection coating to minimise losses at interfaces with air.

Surfaces of the reflector (4) and the optical layer (5) which are in contact with the sample gas may be coated with materials which modify the surface energy. Hence, when water condensate from breath condenses on these surfaces, in the case of high surface energy modifiers, the water condensate forms a thin film rather than a droplet or droplets which potentially scatter and therefore reduce the IR radiation impinging on the detector (3). High surface energy materials for coating the surfaces may be, but are not limited to, hydroxyl and carboxyl containing hydrocarbon thiols. Hydroxyl and carboxyl containing hydrocarbon thiols may be particularly suitable for coating a gold surface to form a self-assembled mono-layer. Poly-ethylene oxide or an amine of cyano containing polymers may be deposited on the surfaces of both the reflector (4) and the optical layer (5). In the case of low surface energy modifiers, the water condensate forms droplets that bead up and fall from the window, or in the case of the reflector (4) coat less of the reflector (4) and so have less effect on the signal. Low surface energy materials may be, but are not limited to fluoro-carbon containing molecules. Fluoro-carbon thiols may be particularly suitable for coating a gold surface using a self-assembled mono-layer.

In addition or in place of surface energy modifying materials, the reflector (4) and/or optical layer (5) which are in contact with the sample gas may be heated so that the surface temperature is high enough to prevent condensation on the reflector (4) and/or the optical layer (5).

The distance between the optical layer (5) and the emitter (2)/detector (3) pair may be kept as small as practical in order to minimise any sampling of gas surrounding the breath tube (1). Preferably, this distance may be less than 1 cm, more preferably less than 1 mm, or even more preferably less than 0.1 mm. In this example, this distance is typically less than 0.1 mm. In this example, a gap is provided between the optical layer (5) and the emitter (2)/detector (3) pair. It will be appreciated that the optical layer (5) may alternatively be in contact with the emitter (2)/detector (3) pair. Furthermore, the optical layer (5) may comprise a plurality of layers between emitter (2) and reflector (4) and/or between detector (3) and reflector (4), respectively.

The emitter (2)/detector (3) pair may be mounted on a printed circuit board (6) which may incorporate high precision locating lugs for locating pins (8) that are incorporated into the injection moulded breath tube (1). This may allow for a high precision alignment of the emitter (2)/detector (3) pair to the reflector (4) so that high collection efficiency may be achieved.

The printed circuit board (6) may allow for a connection between the emitter (2)/detector (3) pair and the driving circuit.

An electrical connector (7) may be connected to the printed circuit board (6) in order to drive the emitter (2)/detector (3) pair.

The system may be designed such that the whole assembly may be removed from the driving electronics and body of the capnometer, and may be replaced. Therefore, the breath tube assembly comprising reflector (4), optical layer (5) and emitter (2)/detector (3) printed on the circuit board (6) may be disposed after use of the capnometer.

Figure 4:
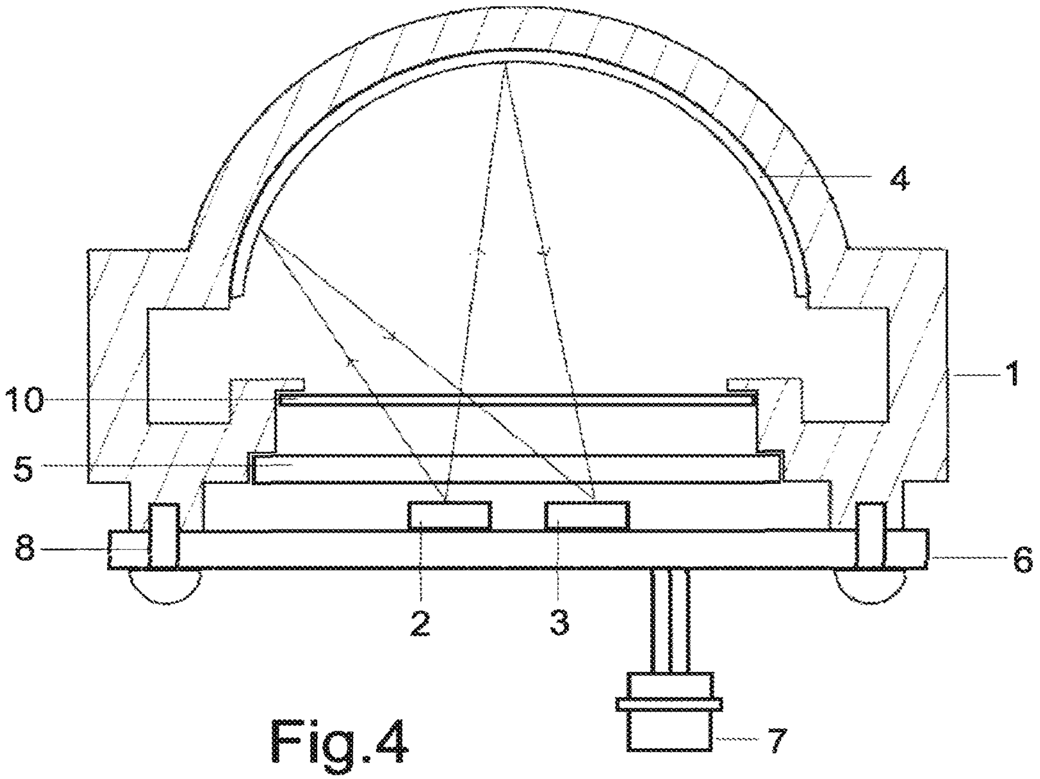
FIG. 4 shows a schematic illustration of a capnometer comprising an IR-transmissive window according to embodiments of the present invention.

FIG. 4 shows a schematic of a capnometer comprising an IR-transmissive window (10) according to embodiments of the present invention. We note that any references to IR-transmissive of any of the components described herein comprises IR-transparent. The IR-transmissivity of any of the component may be above a pre-defined threshold.

In this example, the device comprises an injection moulded breath tube (1) with a coating to form a reflector (4).

Furthermore, in this example, opposite the reflector (4) there is an opening which is covered by a window (10) which has a low attenuation to IR radiation. Materials for such an IR-transmissive window (10) include, but are not limited to, polyolefins such as polyethylene. The thickness of the window (10) is preferably less than 1 cm, more preferably less than 1 mm, or even more preferably less than 100 μm. In this example, the thickness of the IR-transmissive window (10) is less than 100 μm.

The breath tube (1) with reflector (4) and thin IR-transmissive window (10) may incorporate pins (8) which may locate with the printed circuit board (6) containing the emitter (2)/detector (3) pair covered with an optical layer (5) comprising silicon. This may allow for the breath tube (1) to be removable from the capnometer. In this manner, a lower-cost disposable breath tube (1) may be manufactured. It will be appreciated that additionally or alternatively, locator pins (8) may be incorporated into the printed circuit board (6).

An electrical connector (7) may be connected to the printed circuit board (6) in order to drive the emitter (2)/detector (3) pair.

Figure 5:
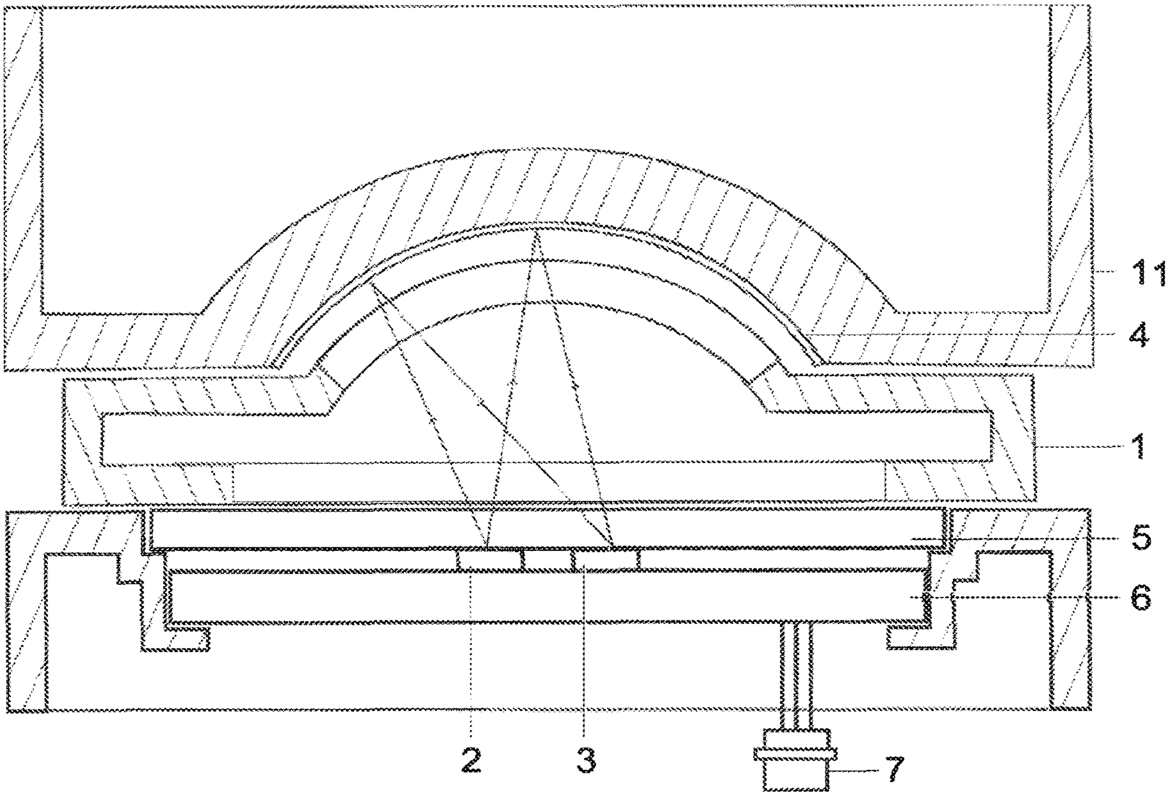
FIG. 5 shows a schematic illustration of a capnometer incorporating a disposable breath tube according to embodiments of the present invention.

FIG. 5 shows a schematic of a capnometer incorporating a disposable breath tube (1). In this example, the capnometer comprises a body (11) of injection moulded high density polymer. The body (11) may contain locating pins (not shown) which align to lugs in the printed circuit board (6). The reflector (4) may optionally be integral to the body (11).

The emitter (2)/detector (3) pair may be arranged on top of the printed circuit board (6). An electrical connector (7) may be connected to the printed circuit board (6) in order to drive the emitter (2)/detector (3) pair.

In this example, an optical layer (5) comprising silicon is disposed on top of the emitter (2)/detector (3) pair.

A breath tube (1) may be interspersed between the moulded body (11) and the printed circuit board (6). The breath tube (1) may comprise windows or IR-transmissive or IR-transparent material.

Therefore, the breath tube (1) in this example may be disposable, allowing for a low-cost production of the breath tube (1).

Figure 6:
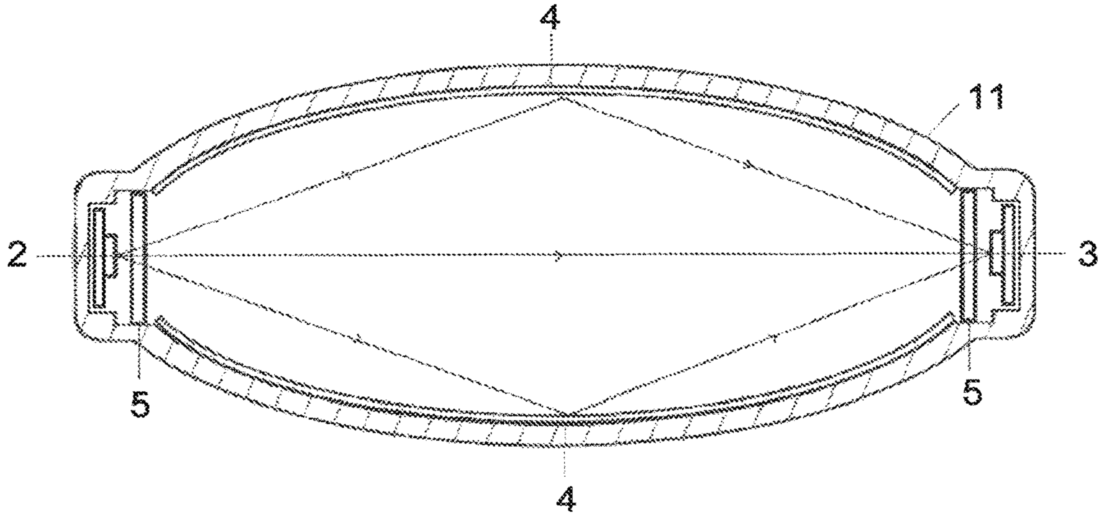
FIG. 6 shows a schematic illustration of a capnometer according to an embodiment of the present invention.

FIG. 6 shows a schematic of a capnometer wherein the emitter (2) and detector (3) are arranged on opposite sides of the air flow region. This embodiment exploits a reflecting geometry, wherein the emitter (2), the detector (3) and the reflector (4) are arranged such that IR light emitted by the emitter (2) passes through the air flow region via the reflector (4) to the detector (3).

In this configuration, the reflector (4) may be arranged on one side of the air flow region only, or, alternatively, on both sides of the air flow region as shown in FIG. 6.

Furthermore, the embodiment of FIG. 6 may allow using either a reflecting geometry, or a non-reflecting geometry in which IR light passes through the air flow region without being reflected by the reflector (4), or a combination of reflecting and non-reflecting geometries.

In this example, emitter (2) and detector (3) may be mounted in a breath tube (not shown in FIG. 6), which may be removable from the capnometer. Alternatively, emitter (2) and detector (3) may be mounted on two inner surfaces of the body (11) of the capnometer on opposing sides facing the air flow region. Emitter (2) and detector (3) may be integral to the body (11) of the capnometer.

As shown in FIG. 6, optical layers (5) which may comprise silicon, may be arranged between the air flow region and the emitter (2) and the detector (3), respectively. It will be appreciated that only a single optical layer (5) may be arranged, either between the air flow region and the emitter (2), or between the air flow region and the detector (3). In this example, optical layers (5) are arranged between both the air flow region and the emitter (2) as well as the air flow region and the detector (3). As outlined above, (an) optical layer(s) (5) may improve a collection efficiency of IR light emitter by the emitter (2) onto the detector (3).

Figure 7:
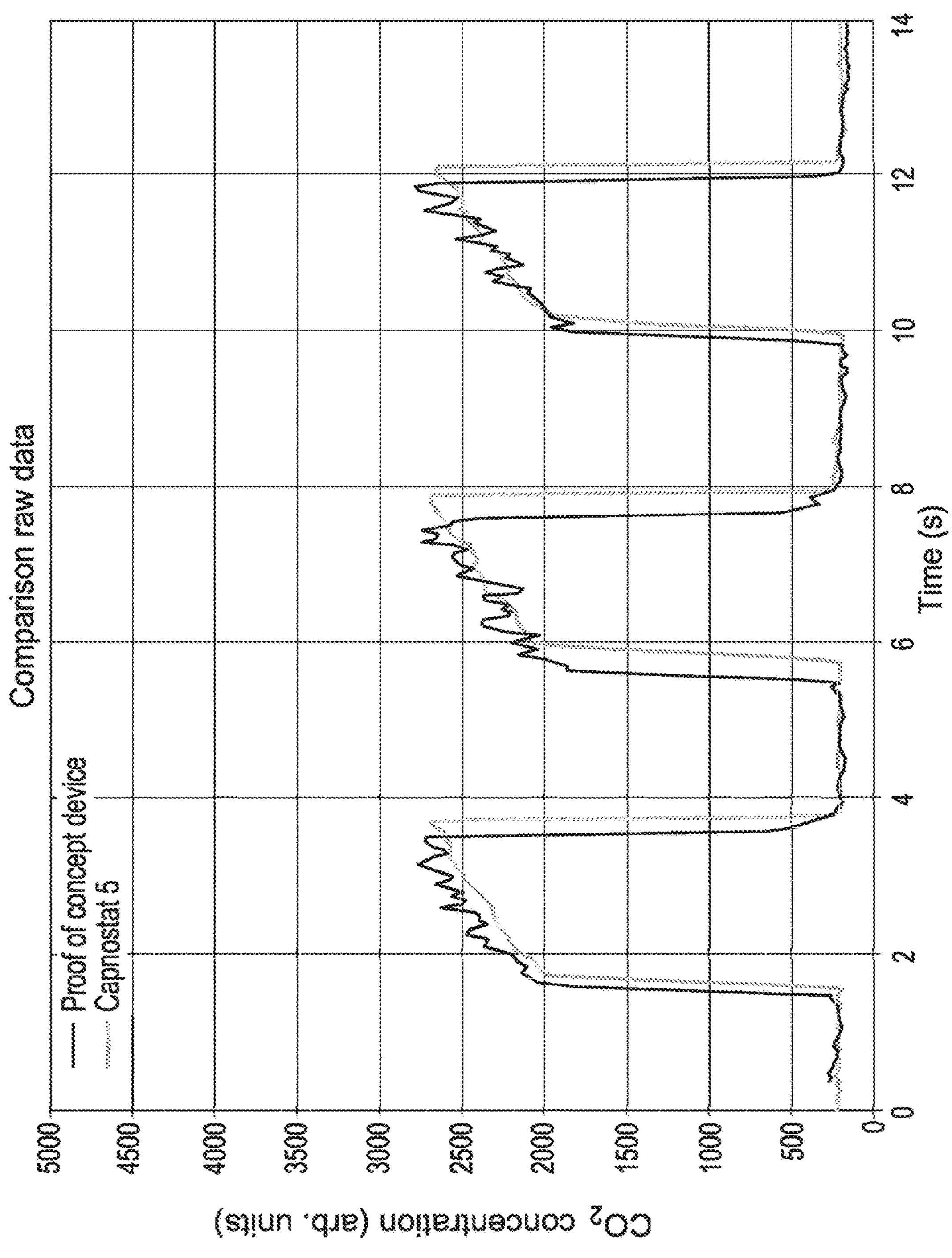
FIG. 7 shows $CO_2$ concentration as a function of time.

FIG. 7 shows measurements of $CO_2$ concentration as a function of time performed with a capnometer as described in embodiments herein, as well as with a standard Capnostat® 5 capnometer, respectively. In this example, three inspiration/expiration cycles of a patient have been recorded with each of the above-specified devices over a time period of 14 seconds.

It can be seen that measurements taken with the capnometer described herein show some minor fluctuations in the detected $CO_2$ concentration compared to the slightly more stable Capnostat® capnometer. However, generally, the signals detected with each of the capnometers substantially coincide with regard to their frequency, amplitude, rise and fall time of a signal, and other characteristics. This example shows a proof of concept of the capnometer described in this specification.

In embodiments described herein, there is a problem of contamination of the reflective surface and/or any IR-transmissive windows/components. Contamination may reduce the signal received by the detector (3) and it may appear as an increase in $CO_2$ level even if no change has actually occurred. One method to mitigate this is to monitor the inspiration phase of the breath cycle where fresh air with low $CO_2$ levels is passed through the sampling area. Typically, the $CO_2$ concentration is approximately 450 ppm. It will be appreciated that the threshold may vary and may preferably be adjusted depending on conditions of the area surrounding the device. If the measured $CO_2$ level is higher than the threshold, the system may indicate that the measurement is void. A correction to the measured $CO_2$ level may be made.

In an alternative embodiment, the capnometer comprises an additional emitter (2) which emits radiation centered around less or more than 4.26 μm, but still within the detecting range of the detector (3). The two emitters (2) may be pulsed in opposite phases so that the detector (3) may detect the two emitters (2) at separate points in time. In this way, any scattering of radiation due to contamination may be similar between the two emitter radiations. A correction may be applied to the signal from the emitter (2) emitting IR-light centred at or around 4.26 μm. It will be appreciated that alternatively or additionally, the signal detected by the detector (3) may be corrected based on the determined contamination.

In embodiments described herein, there is a problem of achieving accurate calibration of the system. This is particularly the case where a replaceable breath tube (1) is employed since there is a possibility of small variations in alignment. The device may be calibrated assuming the background $CO_2$ level is known. This might be the case if the air is ambient air. Alternatively, the $CO_2$ level may be obtained from a different information source.

Alternatively, a breath tube (1) incorporating a gas of known $CO_2$ level may be used for calibrating the device. The breath tube (1) may comprise end caps which may have removable elements such that after calibration the removable elements may be peeled off and the device is ready to use.

The effect of an incorrect zero value may have a large impact on the calculated $CO_2$ concentration at end tidal values found in human breath—typically around 5%. For example, an error of approximately 0.3% in the signal level at the zeroing point will cause a ~10% variation in the calculated output at 5% $CO_2$ concentration. Therefore, if a change to the signal of the capnometer occurred due to any other factor apart from the $CO_2$ concentration, that causes the output as measured at the original zeroing point to change by more than 0.3%, then larger than 10% errors may occur in the value of end tidal $CO_2$ concentration. Hence, in order to achieve an accurate capnogram without a reference channel, it is important to monitor the stability of the $CO_2$ background level.

Figure 8:
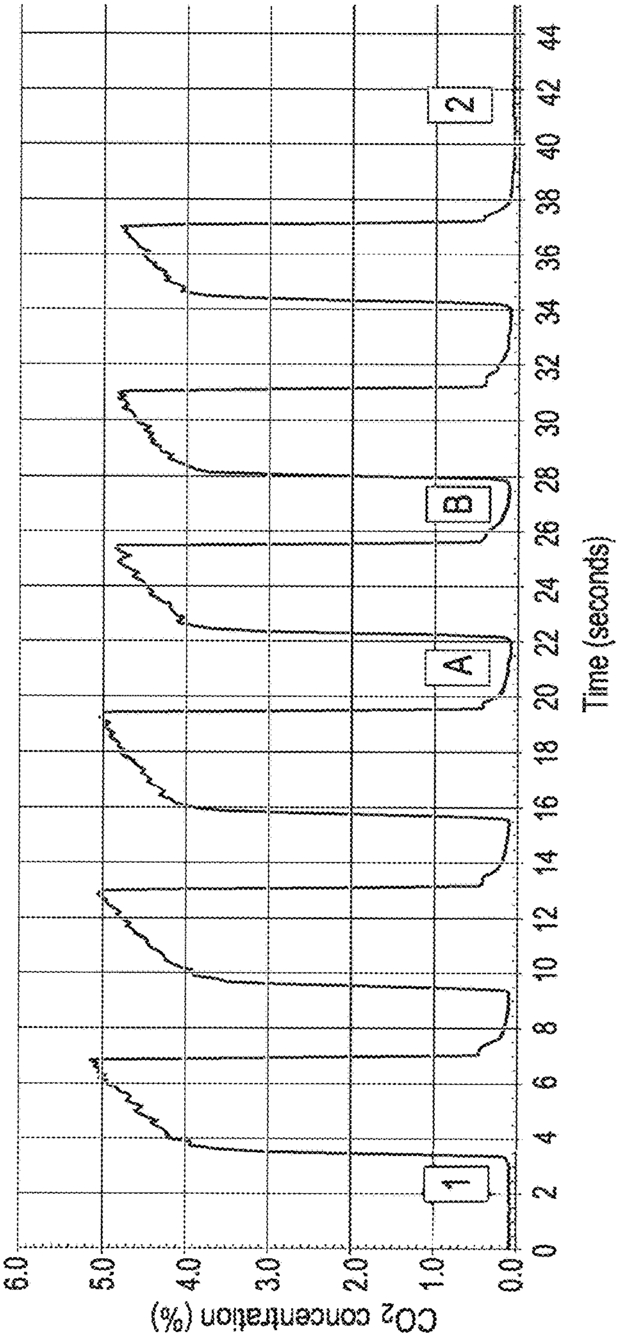
FIG. 8 shows $CO_2$ concentration as a function of time and indications when $CO_2$ background level measurements are taken in this example.

FIG. 8 shows $CO_2$ concentration as a function of time. A typical capnogram of human breathing is indicated.

Before breathing starts, there is a flat baseline level and zeroing can be made at this point (point 1 in FIG. 8). The breathing then starts with the typical breath profile showing a rapid rise in $CO_2$ concentration to the end tidal plateau, the highest point being the end tidal peak at around 5% before inhalation and a rapid decrease back to a background level occurs.

After breathing has stopped, the device should go back to the same background level as at the start (if no change in $CO_2$ background level has occurred), which is recorded at this point (point 2 in FIG. 8). However, if the background level is different at points 1 and 2, this indicates a drift in the $CO_2$ background level of air surrounding the capnometer. By making the assumption that, for example the drift occurred linearly over the breath sample, a correction can be made to the capnogram by carrying out a linear correction.

Figure 9:
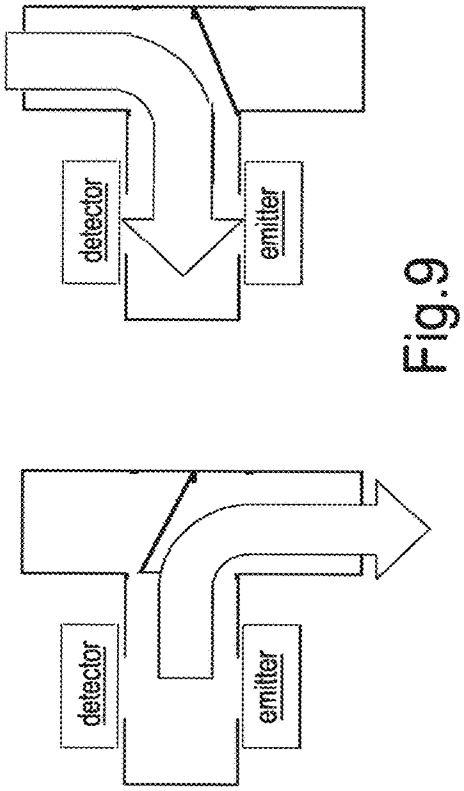
FIG. 9 shows a schematic of parts of a capnometer comprising a diverting valve according to embodiments of the present invention.

FIG. 9 shows a schematic of parts of a capnometer with a diverting valve.

The value of the $CO_2$ background level can be made, for example, between breaths at points A and B (see FIG. 8). A correction can be applied based on the $CO_2$ background level change that occurs between these points. For this to occur, the deadspace (space in the capnometer at which air exhaled by patient is not entirely or nearly entirely replaced subsequently by air inhaled by the user) in the capnometer needs to be minimised so that the capnometer is fully (or at least almost fully) flushed with inhaled air. In this example, a diverting valve is placed in the output of the capnometer so that air can be inhaled from the opposite side to the exhalation, as shown in FIG. 9, to reduce the impact of inhaling exhaled air.

No doubt many other effective alternatives will occur to the skilled person. It will be understood that the invention is not limited to the described embodiments and encompasses modifications apparent to those skilled in the art and lying within the spirit and scope of the claims appended hereto.

The invention claimed is:

1. A capnometer for detecting a concentration of a component in a gas provided by a patient, said capnometer comprising:

a body;

a printed circuit board coupled to the body and comprising:

a mid-IR semiconductor emitter configured to provide IR light at a wavelength in a range 3-5 μm; and a mid-IR semiconductor detector configured to detect said IR light;

an optical layer coupled to the body, oriented parallel to a surface of the printed circuit board, and disposed within one millimeter of said emitter and said detector;

a concave reflector coupled to the body, disposed opposite the optical layer, and configured to reflect said IR light emitted by said emitter toward said detector;

a removable breath tube configured to be inserted within the body between the optical layer and the concave reflector in a direction which is parallel to the surface of the printed circuit board, the removable breath tube comprising:

a first mid-IR transmissive portion configured to be aligned with the optical layer when the removable breath tube is inserted within the body;

a second mid-IR transmissive portion configured to be aligned with the concave reflector when the removable breath tube is inserted within the body; and an air flow region configured to pass the gas to and/or from a lung of the patient when the removable breath tube is inserted within the body, said air flow region including a reduction in cross-sectional area in a sampling area where said IR light passes through said air flow region sufficient to accelerate the gas through the sampling area.

2. The capnometer as claimed in claim 1, wherein said detection of said concentration of said component in said gas comprises detecting a temporal variation of said concentration.

3. The capnometer as claimed in claim 1, wherein the optical layer comprises silicon and is disposed on top of the emitter and the detector.

4. The capnometer as claimed in claim 1, wherein said emitter is configured to provide said IR light at two or more different wavelengths in the range 3-5 μm, and wherein said detector is configured to detect said two or more different wavelengths.

5. The capnometer as claimed in claim 1, further comprising a reflector mounting for supporting said reflector.

6. The capnometer as claimed in claim 1, further comprising a memory to store a level data output.

7. The capnometer as claimed in claim 1, wherein said component is $CO_2$.

8. The capnometer as claimed in claim 1, wherein said emitter comprises a III-V mid-IR semiconductor emitter.

9. The capnometer as claimed in claim 1, wherein said detector comprises a III-V mid-IR semiconductor detector.

10. The capnometer as claimed in claim 1, wherein said reflector comprises a reflective metal film coated with an organic layer.

11. The capnometer as claimed in claim 1, wherein said emitter comprises a plurality of emitters, and wherein each of said plurality of emitters emits light centred at a different, respective wavelength.

12. The capnometer as claimed in claim 1, wherein said detector comprises a plurality of detectors, and wherein each of said plurality of detectors detects light at a different, respective range of wavelengths.

13. The capnometer of claim 1, further comprising a diversion device for blocking one of a first and a second air-flow path in the capnometer at a time, said diversion device comprising a diverting valve which is controlled by inhalation/exhalation of said gas by said patient, wherein said first air-flow path connects an inhaling/exhaling portion of the capnometer at which said patient inhales/exhales air and an intake portion of said capnometer through which air enters said capnometer, and wherein said second air-flow path connects said inhaling/exhaling portion and an exit portion of said capnometer at which air exits said capnometer.

14. An inhaler comprising:
a capnometer according to claim 1, wherein said capnometer is configured to monitor a $CO_2$ level in air inhaled through or exhaled through said inhaler.

* * * * *